US009632051B2

(12) United States Patent
Nivet et al.

(10) Patent No.: US 9,632,051 B2
(45) Date of Patent: Apr. 25, 2017

(54) MULTI-ELECTRODE SENSOR FOR DETERMINING THE GAS CONTENT IN A TWO-PHASE FLOW

(75) Inventors: Philippe Nivet, Cantiers (FR); Alain Bruere, Chatenay Malabry (FR); Didier Matarin, Saint Marcel (FR)

(73) Assignees: SNECMA, Paris (FR); CENTRE NATIONAL D'ETUDES SPATIALES, Paris (FR)

( * ) Notice: Subject to any disclaimer, the term of this patent is extended or adjusted under 35 U.S.C. 154(b) by 380 days.

(21) Appl. No.: 14/236,811

(22) PCT Filed: Jul. 31, 2012

(86) PCT No.: PCT/FR2012/051802
§ 371 (c)(1),
(2), (4) Date: Mar. 14, 2014

(87) PCT Pub. No.: WO2013/017795
PCT Pub. Date: Feb. 7, 2013

(65) Prior Publication Data
US 2014/0203824 A1 Jul. 24, 2014

(30) Foreign Application Priority Data
Aug. 2, 2011 (FR) .................................... 11 57084

(51) Int. Cl.
*G01N 27/22* (2006.01)
(52) U.S. Cl.
CPC ................................. *G01N 27/221* (2013.01)
(58) Field of Classification Search
CPC ............................. G01N 27/221; G01N 27/22
See application file for complete search history.

(56) References Cited

U.S. PATENT DOCUMENTS 2,926,749 A * 3/1960 Oswald ..................... B03C 3/49
55/DIG. 38
3,123,751 A 3/1964 Balsbaugh
(Continued)

FOREIGN PATENT DOCUMENTS

EP 0 936 462 8/1999
JP 10-282032 A 10/1998
(Continued)

OTHER PUBLICATIONS

Baranov et al., RU 2045091 C1, Sep. 1995, English Translation.*
(Continued)

*Primary Examiner* — Melissa Koval
*Assistant Examiner* — Haidong Zhang
(74) *Attorney, Agent, or Firm* — Oblon, McClelland, Maier & Neustadt, L.L.P.

(57) ABSTRACT

A sensor for determining gas content of a two phase fluid flowing in a flow line, the sensor including a sleeve configured to be arranged in the flow line in a stream of fluid. The sleeve includes a plurality of measurement electrodes that, in pairs, define a plurality of subdivision spaces subdividing a flow section of the sleeve. The sensor also includes switch and measurement members coupled to the measurement electrodes to control switching of each subdivision space of the sleeve between a measuring state and a non-measuring state. The switch and measurement members are configured to selectively switch the state of each of the subdivision spaces independently of one another.

14 Claims, 4 Drawing Sheets

(56) References Cited

U.S. PATENT DOCUMENTS

| | | | |
|---|---|---|---|
| 3,421,077 | A | 1/1969 | Liu et al. |
| 4,063,153 | A | 12/1977 | Dechene et al. |
| 4,074,184 | A | 2/1978 | Dechene et al. |
| 4,082,994 | A | 4/1978 | Newton |
| 4,555,661 | A | 11/1985 | Benson et al. |
| 4,835,456 | A | 5/1989 | Liu et al. |
| 5,861,755 | A | 1/1999 | Moerk et al. |
| 6,412,351 | B1 | 7/2002 | Zunft |
| 2002/0021731 | A1* | 2/2002 | Bragin .................... H01S 3/225 372/57 |
| 2008/0118410 | A1* | 5/2008 | Furukawa .......... B01D 46/0013 422/186.03 |

FOREIGN PATENT DOCUMENTS

| | | | |
|---|---|---|---|
| JP | 11-512831 A | | 11/1999 |
| JP | 2008-534988 A | | 8/2008 |
| RU | 2045091 C1 | * | 9/1995 |

OTHER PUBLICATIONS

Office Action mailed May 19, 2016, in Japanese Patent Application No. 2014-523371 (in English).
International Search Report Issued Oct. 16, 2012 in PCT/FR12/051802 Filed Jul. 31, 2012.

* cited by examiner

MULTI-ELECTRODE SENSOR FOR DETERMINING THE GAS CONTENT IN A TWO-PHASE FLOW

The present invention relates to the field of sensors for determining the gas content of a two-phase fluid flowing in a flow line installed in any industrial application, e.g. in a rocket or other engine.

Knowledge of the volume fraction of gas present in a liquid has numerous applications, in particular applications in the aerospace field.

For example, the turbopumps of rocket engines are fed with cryogenic propellants, in particular liquid hydrogen and liquid oxygen. At the inlets to the pumps, the presence of gas in the liquid disturbs fluid flows, with the risk of creating cavitation phenomena that can lead to the turbopumps racing. It is consequently of great importance in the context of such an application to be able to identify and measure the presence of gas in the feed propellants.

Conventional capacitive sensors are known that have two electrodes suitable for being arranged in a pipe, in the flow of a two-phase fluid flowing in the pipe. A first one of the two electrodes constitutes an anode in the form of a cylindrical core, while the other electrode constitutes a cathode forming a portion of a segment of the pipe.

Such conventional capacitive sensors are configured to measure the relative permittivity (or dielectric constant) of the two-phase fluid flowing in the pipe between the cathode and the anode, thus making it possible to determine the volume fraction of gas present in the liquid phase of the fluid.

More precisely, the dielectric constant of a fluid depends directly on its refractive index. It is found that the refractive index of a fluid in the gaseous state is generally slightly different from the refractive index of the same fluid when in the liquid state, such that with prior knowledge of these two refractive indices and using such a capacitive sensor arranged in the flow duct to measure the dielectric constant of the fluid flowing in a two-phase state, it becomes possible to determine the content of gas bubbles present in the liquid phase of the fluid.

Nevertheless, the gas bubble contents as measured by such conventional sensors are inaccurate compared with the real contents of bubbles that form in the flow section of the pipe segments in which the sensors are installed.

This becomes particularly problematic when the gas bubble contents as measured by such conventional sensors correspond to contents that are averaged across the entire flow section of the sensor, such that the contents as measured do not make it possible to detect potential proliferations of gas bubbles that may be very localized.

Consequently, there is a pressing need to develop a sensor that is capable of accurately measuring both the mean and the local contents of gas bubbles forming within a given flow section.

The present invention proposes providing such a sensor.

More precisely, a sensor in the meaning of the present invention makes it possible to determine the gas content of a two-phase fluid flowing in a flow line, the sensor comprising a sleeve suitable for being arranged in the flow line, in the stream of fluid. The sleeve of the sensor comprises a plurality of measurement electrodes spaced apart from and in register with one another so that in pairs they define a plurality of subdivision spaces subdividing the flow section of said sleeve. The sensor also comprises switch and measurement members that are coupled to the measurement electrodes in such a manner as to cause each subdivision space of the sleeve to switch between a measuring state in which said members apply an excitation electrical signal between the two adjacent measurement electrodes defining a subdivision space under consideration and measure a value representative of the reception electrical signal resulting from applying said excitation electrical signal in order to determine the gas content of the fluid that is associated with said representative value, and a non-measuring state. The switch and measurement members are configured to selectively switch the state of each of the subdivision spaces independently of one another.

It can be understood that the sleeve of the sensor thus has three or more measurement electrodes that enable the flow section of said sleeve to be subdivided into two or more subdivision spaces, which spaces correspond to the inter-electrode spaces that are defined by the measurement electrodes in pairs.

Thus, for given flow sections and all other things remaining equal, the inter-electrode distance in the sleeve of a sensor of the present invention is smaller than that of a conventional sensor of the above-described type having two electrodes, thus making it possible to measure signals with a better signal-to-noise ratio, and thus signals that are more accurate.

Furthermore, the presence of a plurality of subdivision spaces that result from fitting the sensor with a larger number of measurement electrodes is advantageously used in the present invention in order to be able to measure accurately the gas bubble contents that form locally in only one or in some of the subdivision spaces, which spaces are selected by switching between the measuring and non-measuring states, as can be performed arbitrarily and in independent manner for each of the subdivision spaces of the sleeve of the sensor.

Furthermore, to ensure that a subdivision space under consideration adopts its non-measuring state, it is possible in particular to configure the switch and measurement members so as to prevent electrical excitation being established between the two adjacent measurement electrodes defining said subdivision space under consideration.

Several alternatives may be used to enable a subdivision space under consideration to adopt its non-measuring state.

Thus, in a first advantageous alternative, the switch and measurement members apply the same electric potential to the two adjacent measurement electrodes that define the subdivision space under consideration in order to cause said space to adopt its non-measuring state.

It can thus be understood that so long as the subdivision space remains in its non-measuring state, the potential difference across the terminals of the two measurement electrodes that define it is maintained at a zero value (in practice, this potential difference is maintained at a value that is as close to zero as is possible when using the switch and measurement members with which the sensor is fitted).

As a result, said two adjacent measurement electrodes are held in a forced state that prevents any electrical excitation being established between those two electrodes.

In another advantageous alternative, the switch and measurement members interrupt all electrical connections between the two adjacent measurement electrodes defining the subdivision space under consideration in order to cause said space to adopt its non-measuring state.

Under such circumstances, the switch and measurement members can reestablish this electrical connection when the subdivision space adopts its measuring state, so as to allow electrical excitation to be established between the two adjacent measurement electrodes defining said space.

Advantageously, the excitation electrical signal is a voltage that varies periodically under steady conditions, preferably with a mean value of zero. In particular, it is possible to use a voltage presenting a waveform that is sinusoidal, squarewave, triangular, a train of pulses, etc.

Under such circumstances, the reception electrical signal (or response signal) that results from applying said excitation electrical signal also varies periodically, with amplitude and/or period and/or phase shifts relative to the excitation electrical signal that depend(s) on the dielectric constant of the fluid flowing in the subdivision space under consideration.

Nevertheless, in the context of the present invention, it is also possible to apply a variable voltage between the two adjacent measurement electrodes that define the subdivision space under consideration, which voltage is variable under non-steady conditions, or a fixed voltage, or a signal of any other kind, providing only that the excitation electrical signal gives rise at at least one given time interval to charges being moved between the two measurement electrodes of the subdivision space under consideration, thereby making it possible to determine the dielectric constant of the fluid flowing in the subdivision space under consideration.

Furthermore, the switch and measurement members may advantageously be configured in such a manner that said representative value as measured by said members is representative solely of the reception electrical signal that results from applying the excitation electrical signal between the two measurement electrodes defining the subdivision space under consideration.

It can thus be understood that said representative value is not influenced by the gas content in the fluid flowing in the or each other adjacent subdivision space, with this applying regardless of the switching state in which that adjacent space is to be found.

In an advantageous alternative, the switch and measurement members may be configured so that said representative value has a first component that is representative of the reception electrical signal that results from applying the excitation electrical signal between the two adjacent measurement electrodes defining the subdivision space under consideration, together with a second component representative of the reception electrical signal that results from applying any excitation electrical signal that might be applied between the two adjacent measurement electrodes defining some other subdivision space adjacent to the space under consideration.

By way of example, this may be done by said representative value being measured at the terminals of a two-terminal circuit, preferably a resistive circuit, that is coupled to the measurement electrode that is common to said subdivision space under consideration and to said adjacent space, and to a line of the sensor at a fixed potential, in particular at its ground potential.

Under such circumstances, and when it is selected to apply an excitation electrical signal that varies periodically under steady conditions, said representative value measured at the terminals of said two-terminal circuit corresponds to its impedance.

Advantageously, the switch and measurement members sequentially switch the state of at least one of the subdivision spaces at least once during a measurement cycle.

It can be understood that it is thus possible to take advantage of the fact that the switch and measurement members can switch each of the subdivision spaces of the sleeve of the sensor independently from one another in order to define a measurement cycle during which at least one of those subdivision spaces is switched sequentially one or more times between states.

Under such circumstances, it is possible to define any switching sequence that is to be performed during such a measurement cycle.

For example, it may be advantageous for each subdivision space to adopt its measuring state at least once during the measurement cycle.

Under such circumstances, it is possible to scan through each of the subdivision spaces of the sleeve of the sensor during the measurement cycle, thus making it possible to establish an accurate map of gas bubble distribution within the flow section of said sleeve.

Likewise, during the measurement cycle, it may be advantageous for the sensor to adopt at least one configuration in which at least a first one of the subdivision spaces adopts its measuring state while at least one other subdivision space adjacent to the first (and preferably each of them) adopts its non-measuring state.

This configuration is particularly advantageous when the switch and measurement members are also configured so that the representative value they measure comprises first and second components representative of reception electrical signals associated respectively with said first subdivision space and with said adjacent subdivision space, as described above. With the sensor in this configuration, said second component of the measured representative value is zero (in practice as close to zero as is possible with the switch and measurement members) in this non-measuring state of said adjacent subdivision space. As a result, the measured representative value makes it possible to obtain directly the dielectric constant of the fluid flowing specifically in said first subdivision space, and to do this without the gas content of the fluid flowing specifically in said other subdivision space having any influence on the measurement of said representative value.

In addition, it may be advantageous at a first time interval of the measurement cycle for at least a first one of the subdivision spaces to adopt its measuring state while a second subdivision space adjacent to the first adopts its non-measuring state, and at a second time interval (before or after said first time interval) of said cycle for at least said first space to remain in its measuring state while said second space adopts its measuring state.

Under such circumstances, it is preferable for each subdivision space that is adjacent to said first space or to said second space to remain in an unchanging measuring or non-measuring state (preferably the non-measuring state) during the first and second time intervals.

Thus, when the representative value associated with said first subdivision space is also selected to comprise both first and second components representative of reception electrical signals associated respectively with said first and second subdivision spaces, as described above, then this representative value makes it possible at the first time interval to determine the dielectric constant of the fluid flowing specifically in said first space, while at the second time interval this representative value makes it possible to determine the dielectric constant of the fluid flowing in the combined space constituted by said first and second spaces taken together.

Under such circumstances, the dielectric constant of the fluid flowing specifically in said second subdivision space may advantageously be deduced from the two preceding measurements by subtracting the dielectric constant obtained at the first time interval from the dielectric constant obtained at the second time interval.

It can be understood that the switch and measurement members can thus advantageously comprise a measurement circuit that is used in common for the first and second subdivision spaces and that makes it possible to determine the content of gas bubbles that form specifically in said first subdivision space and specifically in said second subdivision space, while requiring only one change of state to be switched between said first and second time intervals of the cycle, namely the state of said second space.

Advantageously, at least a first one of the subdivision spaces adopts its measuring state a greater number of times than at least one other one of the subdivision spaces during the measurement cycle.

It can be understood that it is thus possible to monitor certain subdivision spaces of the sensor more attentively, said spaces being considered as being more subject to the formation of gas bubbles than other spaces of the sensor that are considered to be less problematic.

Advantageously, the measurement cycle is performed repetitively, preferably periodically.

It can thus be understood that it is possible to track variation in the spatial distribution of gas bubbles in one or more of the subdivision spaces of the sleeve of the sensor.

Advantageously, the sleeve of the sensor includes guard electrodes that extend the ends of the measurement electrodes while being electrically separate therefrom, and that are coupled to the switch and measurement members in such a manner that the guard electrodes are at all times at the same electric potential as the measurement electrodes that they extend respectively.

It can be understood that these guard electrodes serve to prevent edge effects that would otherwise significantly affect the response of the measurement electrodes to the electrical excitation to which they are subjected, in the event of the inter-electrode distances not being negligible compared with the dimensions of the measurement electrodes.

Furthermore, when it is selected to excite the measurement electrodes of the sensor with excitation electrical signals under steady varying conditions, in order to improve the accuracy of measurements, it is preferable to ensure that the frequencies, the phases, and the amplitudes of the electrical potentials that are applied to the guard electrodes are identical at all times to the frequencies, the phases, and the amplitudes of the electrical potentials of the respective measurement electrodes that they extend.

Advantageously, the sensor may optionally include one or more structural elements suitable for co-operating with the measurement electrodes in order to hold said electrodes apart and in register with one another.

Advantageously, the measurement electrodes are spaced apart from one another by spacers at least partly made of electrically insulating material, e.g. made of polytetrafluoroethylene (PTFE).

Advantageously, each sleeve of the sensor also includes guard electrodes that may be held apart from one another so as to extend the corresponding measurement electrodes by means of these spacers.

Advantageously, the spacers have passages into which connection wires are inserted so as to provide the coupling between the measurement electrodes (and their guard electrodes, if any) and the switch and measurement members.

As a result the sleeve of the sensor can thus advantageously be arranged in the flow line of the fluid, e.g. optionally inside a pipe segment of said flow line or between two such segments, while the switch and measurement members are suitable for being arranged outside said flow line and remotely therefrom so as to make them more easily accessible for the user of the sensor.

Furthermore, the measurement electrodes (and their guard electrodes, if any) may adopt any suitable shape, providing only that they are capable of extending spaced-apart from and in register with one another so as to act in pairs to define a plurality of subdivision spaces subdividing the flow section of the sleeve of the sensor.

For example, the measurement electrodes (and likewise their guard electrodes, if any) may advantageously be plane and parallel to one another.

This solution is found to be advantageous when the flow section of the flow line is rectangular.

In an alternative that is particularly advantageous given that the section of the great majority of pipe segments used in flow lines is circular, the measurement electrodes (and likewise their guard electrodes, if any) may be coaxial, surrounding one another about a common axis, and presenting a section that is circular in a section plane perpendicular to the common axis.

Under such circumstances, the measurement electrodes (and likewise their guard electrodes, if any) may advantageously be selected equally well to be frustoconical or cylindrical.

Advantageously, the ratio of the diameters of two adjacent measurement electrodes (and of the corresponding guard electrodes, if any) in the section plane lies in the range 1.1 to 3.0, so as to increase the accuracy of these measurements.

The inventors of the present invention have discovered, as a result of theoretical calculations, of experimental work, and of numerous digital simulations they have carried out, that the measured dielectric constant of the fluid also varies in non-linear manner for given contents and sizes of gas bubbles, as a function of the radial distance at which the gas bubbles are formed locally relative to the common axis of the measurement electrodes.

The inventors have been able to determine that this phenomenon is due essentially to the fact that the relative volume occupied by a bubble compared with the volume of the annular space of the sleeve in which the bubble is confined is greater when the location at which the bubble forms is radially closer to the common axis of the sleeve of the sensor.

The inventors have thus found a solution that makes it possible to compensate for this radial dependency of the experimental dielectric constant of the fluid by making provision for the ratio of the diameters of two adjacent measurement electrodes in the section plane to lie specifically in the range 1.1 to 3.0.

Said ratio of the diameters preferably lies more specifically in the range 1.4 to 2.0 so as to further increase the accuracy of the measurements.

Furthermore, in the meaning of the present invention, the sleeve of the sensor may have any number of measurement electrodes greater than or equal to three (e.g. three, four, five, six, seven, or more).

It can be understood that for given flow sections and other things remaining equal, the greater the number of measurement electrodes in the sleeve of the sensor, the smaller the inter-electrode distances of that sleeve and thus the greater the accuracy of the measurements taken.

Nevertheless, in order to ensure that the structure of the sensor remains simple to implement and inexpensive, it is preferable for the sleeve of the sensor to have three to six measurement electrodes.

When using a sensor in which the measurement electrodes are bodies of revolution, the ratio of the diameters in the section plane between the two extreme measurement electrodes of the sleeve of the sensor (i.e. the two measurement electrodes that are furthest apart from each other) may then advantageously lie in the range 5 to 20, as a function of the number of measurement electrodes of said sleeve.

Furthermore, it is advantageous for the ratio of the axial length of the measurement electrodes along their common axis over the diameter of the measurement electrode furthest from said common axis to lie in the range 0.25 to 1. This range of values gives a good compromise between optimizing measurement accuracy and minimizing disturbances to the flow caused by the presence of the sleeve in the flow line.

The invention can be better understood and its advantages appear better on reading the following detailed description of embodiments given as non-limiting examples. The description refers to the accompanying drawings, in which.

A sensor in accordance with the present invention comprises a sleeve 10 and switch and measurement members 50.

In FIGS. 1 to 4, there is shown a non-limiting embodiment of a sleeve 10 in accordance with the present invention.

In the embodiment shown, the sleeve 10 of the sensor has five measurement electrodes 1 to 5 that are spaced apart from and in register with one another so as to define in pairs four subdivision spaces A to D subdividing the flow section of said sleeve 10.

The measurement electrodes 1 to 5 are coaxial, surrounding one another about a common axis defining the axial direction of the sleeve 10, and presenting a circular section in a section plane perpendicular to said common axis.

The measurement electrodes 1 to 5 are cylindrical bodies of revolution.

The outer body of the sleeve 10 defining its flow section forms the measurement electrode 1 that is furthest from the common axis, such that the outer body of the sleeve 10 is generally cylindrical about said common axis as its axis of revolution.

Figure 3:
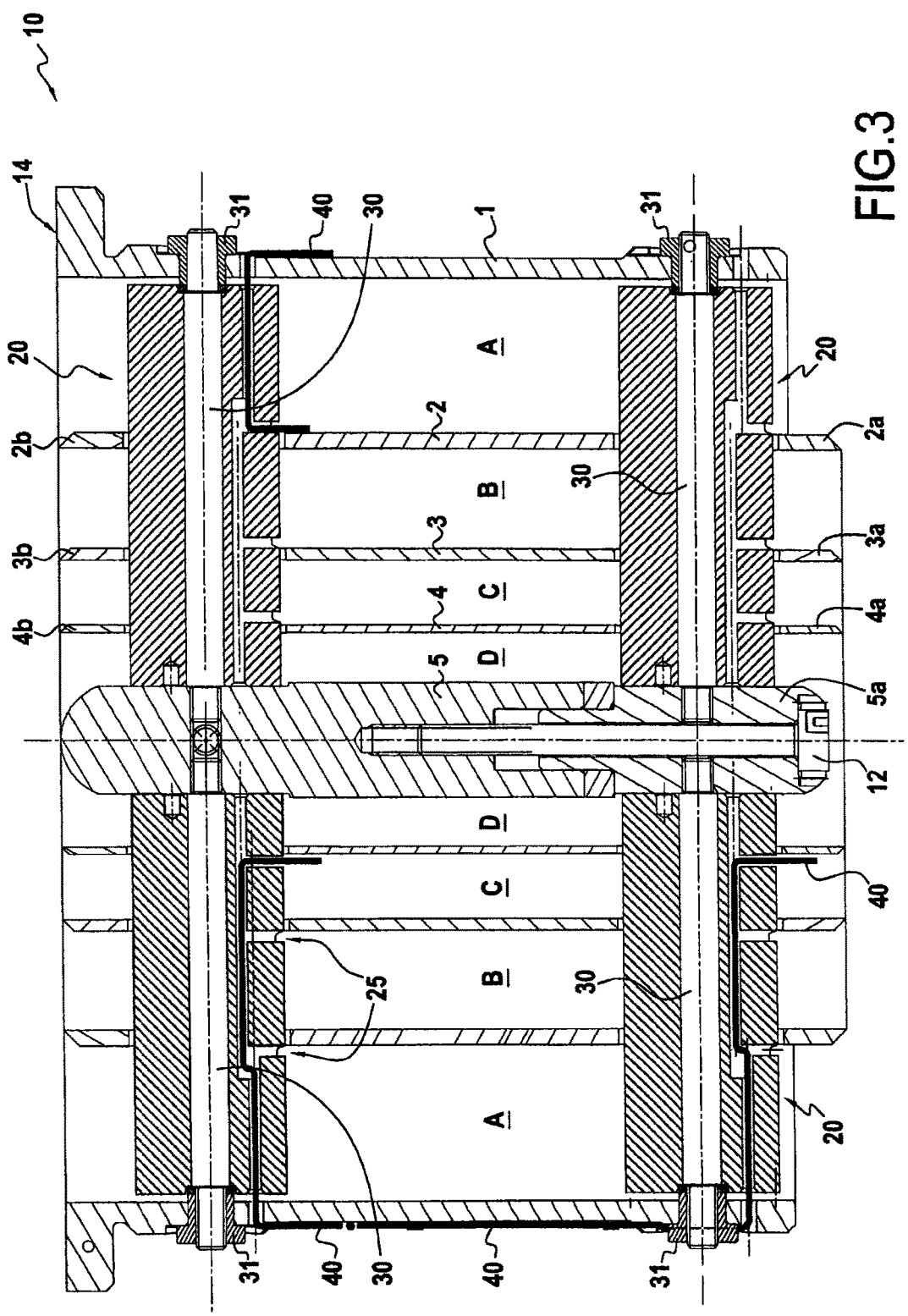
FIG. 3 is a section view of said sleeve on plane III-III of FIG. 2.

The measurement electrode 5 that is closest to the common axis constitutes a cylindrical central core (that may be completely solid, completely hollow, or else merely partially hollow as shown in FIG. 3).

The remaining three measurement electrodes 2, 3, and 4 are intermediate measurement electrodes constituting respective cylindrical rings that extend coaxially between the outer body and the central core of the sleeve 10, and that surround one another.

In this embodiment, the four spaces A to D subdividing the flow section of the sleeve 10, as defined by the five measurement electrodes 1 to 5 in pairs, are annular spaces forming cylindrical volumes of revolution.

In the embodiment shown, the ratio of the diameters of two adjacent measurement electrodes in said section plane lies in the range 1.1 to 3.0, and preferably in the range 1.4 to 2.0 (the diameter of the larger of the two thus being placed in the numerator when calculating the ratio, and the diameter of the smaller of the two being placed in the denominator of said calculation), or indeed it may lie more particularly in the range 1.5 to 1.9.

In particular, in this embodiment, the inside diameter of the first measurement electrode 1 (i.e. the diameter of the inner wall of the outer body of the sleeve 10) is selected to be 121 millimeters (mm) while the outer diameter of the second measurement electrode 2 is 80 mm, such that the ratio of the diameter of the first measurement electrode 1 over the second measurement electrode 2 is about 1.5.

Furthermore, in this embodiment, the inner diameter of the second measurement electrode 2 is selected to be 76 mm (which means that the second electrode in this embodiment has a radial thickness of 2.0 mm), while the outer diameter of the third measurement electrode 3 is 50 mm, such that the ratio of the diameter of the second measurement electrode 2 over the third measurement electrode 3 is about 1.5.

Likewise, in this embodiment, the inner diameter of the third measurement electrode 3 is selected to be 47 mm (which means that said third electrode in this embodiment has a radial thickness of 1.5 mm), while the outer diameter of the fourth measurement electrode 4 is 30 mm, such that the ratio of the diameter of the third measurement electrode 3 over the fourth measurement electrode 4 is about 1.6.

Finally, in this embodiment, the inner diameter of the fourth measurement electrode 4 is selected to be 28 mm (which means that said fourth electrode in this embodiment has a radial thickness of 1.0 mm), while the outer diameter of the fifth measurement electrode 5 (i.e. the outer diameter of the central core) is 15 mm, such that the ratio of the diameter of the fourth measurement electrode 4 over the fifth measurement electrode 5 is about 1.9.

In this embodiment, it also results that the ratio of the inner diameter of the first measurement electrode 1 over the outer diameter of the fifth measurement electrode 5 (i.e. the ratio of the diameters of the two extreme measurement electrodes of the sleeve 10 of the sensor) is about 8.1, i.e. it lies in the above-mentioned preferred range [5, 20].

In addition, in this embodiment, the axial length of the measurement electrodes along their common axis (corresponding in this embodiment to the distance between the two axial ends of the intermediate measurement electrodes 2 to 4) is selected to be 55 mm, such that the ratio of said axial length over the inner diameter of the first measurement electrode 1 is about 0.5, i.e. lying in the above-mentioned preferred range [0.25, 1].

Each measurement electrode 1 to 5 is made of a material that is electrically conductive. In particular, it is thus possible to select brass or indeed stainless steel, where stainless steel is recommended when the sleeve is for incorporating in a cryogenic flow line, e.g. a line carrying a flow of liquid hydrogen (LH2) at a temperature close to 20 K.

Figure 4:
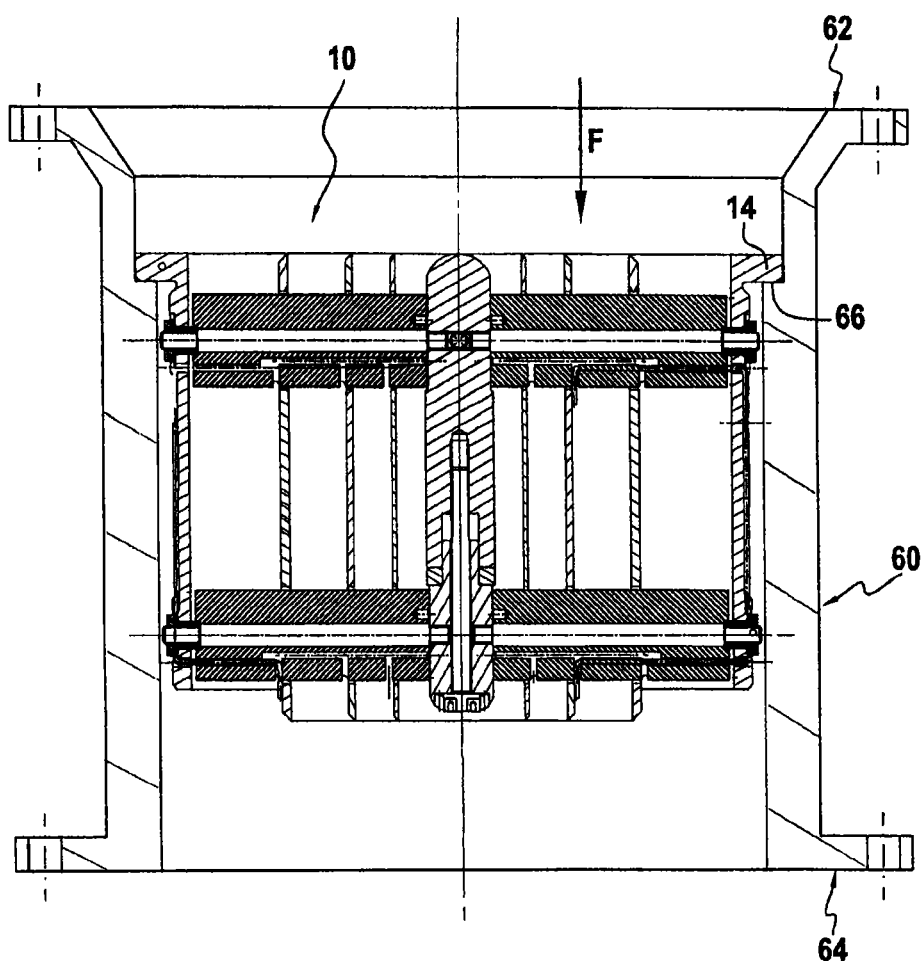
FIG. 4 is a section view of said sleeve on plane IV-IV shown in FIG. 2, and it reveals the possibility of mounting the sleeve in a pipe segment of a flow line.

As shown in particular in FIG. 4, the sleeve 10 of the sensor is suitable for being arranged in any flow line along which a fluid flows, in the stream F of the fluid.

In this embodiment, the sleeve 10 is suitable for being arranged inside a pipe segment 60 forming part of the flow line.

The outer body of the sleeve 10 has a first fastener element suitable for co-operating with a second fastener element forming part of the pipe segment 60 in order to fasten the sleeve 10 in the pipe segment 60.

In particular, the outer body of the sleeve 10 has a flange 14 as its first fastener element that is suitable for pressing against a shoulder 66 constituting the second fastener element that is formed in the inside wall of the pipe segment 60, so as to enable the sleeve 10 to be fastened in the pipe segment 60 by means of screws (not shown) suitable for being received in through holes 16 arranged in the flange 14 (see in particular FIGS. 1 and 2) in order to be engaged in the shoulder 66.

The pipe segment 60 has two flanges 62 and 64 formed respectively at each of its two axial ends in such a manner as to be suitable for being arranged between two other pipe segments (not shown), forming parts of the flow line.

In an advantageous alternative to the embodiment shown, and without going beyond the ambit of the present invention, it is possible to provide for the outer body of the sleeve of the sensor itself to form a pipe segment suitable for being arranged directly between two other pipe segments of the flow line. This alternative makes it possible to reduce the flow restriction caused by the presence of the sleeve of the sensor within the flow line.

The outer body of the sleeve may then advantageously have two flanges analogous to the flanges 62 and 64 forming part of the above-described pipe segment 60.

Figure 2:
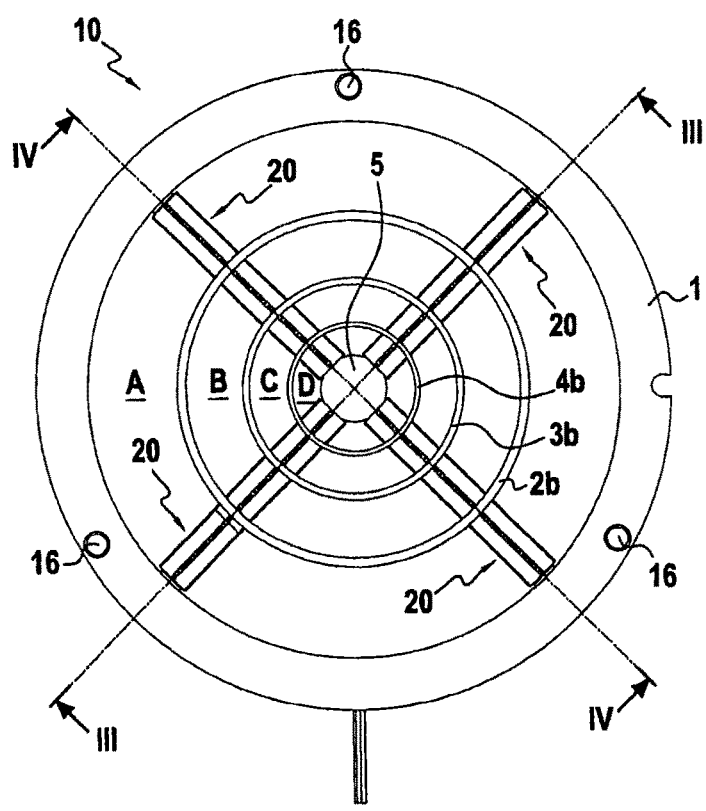
FIG. 2 is a plan view of said sleeve shown in FIG. 1.

Furthermore, and as shown in particular in FIGS. 2 and 3, the measurement electrodes 1 to 5 of the sleeve 10 are spaced apart from one another by spacers 20 that are made entirely out of electrically insulating material, in particular out of PTFE, which spacers are generally in the form of fins.

More particularly, the sleeve 10 has four first spacers 20 at the upstream end of the sleeve 10 that are arranged in a cross around the central core so as to extend in four respective radial directions that are at 90° from one another between the central core and the outer body of the sleeve 10.

The sleeve 10 also has four other spacers 20 at the downstream end of the sleeve 10 that are analogous to the four first spacers, and that extend between the central core and the outer body of the sleeve 10 respectively in the same four radial directions as the radial directions of the four first spacers.

Each spacer 20 is positioned by means of a holder rod 30 that passes through a hole presented in said spacer 20 in order to be fastened to the central core and to the outer body 1 of the sleeve 10.

In the embodiment shown, both ends of each holder rod 30 are threaded so as to enable it to be fastened to the central core by being screwed into a tapped hole therein, and to the outer body 1 by screwing on a nut 31 that presses against the outer wall of the outer body 1, around the edge of a through hole that is present in the outer body 1 so as to allow the holder rod to project outside it in the radial direction of the sleeve 10.

Each spacer 20 comes into abutment against the central core.

Figure 5:
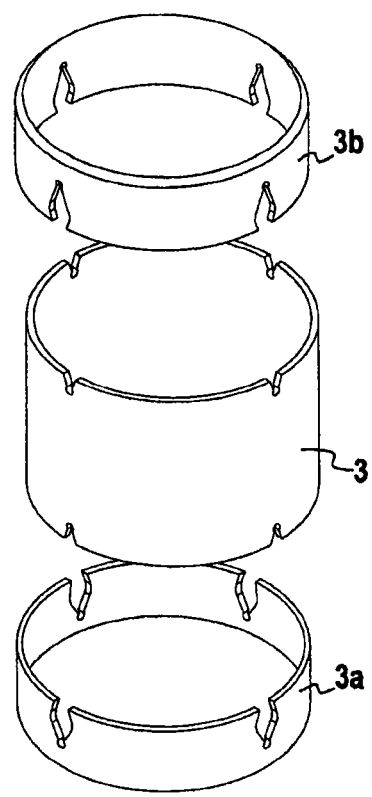
FIG. 5 is a perspective view showing in isolation one of the measurement electrodes of said sleeve together with its two guard electrodes.

Furthermore, as shown in FIG. 5 in particular for the measurement electrode 3, both axial ends of each intermediate measurement electrode 2 to 4 (i.e. the two ends of said electrode that are spaced apart in the axial direction of said electrode) presents four notches that are regularly spaced apart radially and in which the four downstream spacers and the four upstream spacers are respectively suitable for engaging in order to hold said measurement electrodes 2 to 4 spaced apart in the radial direction of the sleeve from the other measurement electrodes 1 to 5 facing them.

In addition, as shown in FIGS. 3 to 5, the sleeve 10 of the sensor has guard electrodes 2a to 4a and 2b to 4b that extend the ends of the measurement electrodes 2 to 4 while being electrically separate therefrom.

More particularly, the two axially opposite ends of the three intermediate measurement electrodes 2 to 4 (i.e. their ends at the upstream and downstream ends of the sleeve 10) are extended at a distance in the axial direction of the sleeve by three respective guard electrodes 2b to 4b at the upstream end and three respective guard electrodes 2a to 4a at the downstream end.

Said upstream guard electrodes 2b to 4b are kept electrically separate from the intermediate measurement electrodes 2 to 4 that they extend by being fastened to the upstream sides of the spacers 20, at the ends of the spacers that are opposite in the axial direction of the sleeve 20 from their ends to which said intermediate measurement electrodes 2 to 4 are fastened.

Likewise, said downstream guard electrodes 2a to 4a are kept electrically separate from the intermediate measurement electrodes 2 to 4 that they extend by being fastened to the downstream ends of the spacers 20 at their ends that are opposite in the axial direction of the sleeve 10 from their ends to which said intermediate measurement electrodes 2 to 4 are fastened.

To do this, and as shown in particular for the two guard electrodes 3a and 3b of the intermediate measurement electrode 3, one of the two axial ends of each guard electrode 2a to 4a, 2b to 4b presents four notches that are regularly spaced apart radially and in which the four corresponding spacers 20 are respectively suitable for engaging in order to hold said guard electrode spaced apart from the measurement electrodes in the axial direction of the sleeve 10 and spaced apart in the radial direction of the sleeve 10 from the other guard electrodes in register therewith.

The guard electrodes 2a to 4a and 2b to 4b are made of material that is electrically conductive, e.g. of brass or preferably of stainless steel when the sleeve 10 is to pass a cryogenic fluid.

In the embodiment shown and in non-limiting manner, the two measurement electrodes 1 and 5 that are furthest apart from each other in the radial direction of the sleeve 10 (i.e. respectively the outer body and the central core of the sleeve 10) are electrically connected to each other and to a line of the sensor that is at a fixed electrical potential, in particular at its ground potential.

In this embodiment, the holder rods 30 are made of electrically conductive material, in particular of brass or of stainless steel, and they establish an electrical connection between the central core, by being engaged therein, and the outer body 1 of the sleeve 10 via the nuts 31 that are also made of electrically conductive material, in particular of brass or of stainless steel.

In the embodiment shown, these two extreme electrodes 1 and 5 act both as measurement electrodes and as guard electrodes.

In the embodiment shown, the outer body 1 is provided as a single piece.

In the embodiment shown, the central core is segmented in the axial direction into a plurality of separate segments suitable for being assembled together in order to form said central core.

In the embodiment shown in FIG. 3, the central core has a first segment 5 that constitutes the measurement electrode 5 proper and in which the upstream holder rods 30 are fastened; a second segment 5a in which the downstream holder rods 30 are fastened; an (optional) shim that is interposed axially between said first and second segments; and an assembly screw 12 suitable for passing through a hole in the second segment 5a in order to engage in a tapped hole in the first segment 5.

Without going beyond the ambit of the present invention, it would nevertheless be possible to provide a central core as a single piece.

Furthermore, and as shown in particular in FIGS. 3 and 4, the spacers 20 present passages 25 through which connection wires 40 are inserted so as to provide both coupling between the measurement electrodes 1 to 5 and the switch and measurement members 50 that are described below, and coupling between the guard electrodes 2a to 4a and 2b to 4b and said switch and measurement members 50.

In particular, the passage 25 in each spacer 20 passes through at least part of said spacer 20 and opens out at a plurality of locations situated in the subdivision spaces A to D of the sleeve 10.

Furthermore, each connection wire 40 coming from outside the sleeve 10 passes to the inside of the outer body 1 by passing through an orifice formed in said body 1 (in particular close to a place where a nut 31 is fastened), in order to penetrate into the inside of a corresponding passage 25 in a corresponding spacer 20 and finally penetrate into the corresponding subdivision space A to D, close to the measurement electrode or the guard electrode with which it is to be connected.

Furthermore, at least one of the elements making up the sleeve 10 of the sensor may advantageously be streamlined so as to minimize head losses in the flow at the inlet and/or the outlet of the sleeve 10.

In the embodiment shown, at least one of the two axial ends of the central core, and in particular its end at the upstream end of the sleeve 10 (given reference 5b in FIG. 1) is rounded in shape.

The axial end of each guard electrode 2a to 4a and 2b to 4b that is remote in the axial direction from the end at which the measurement electrode 2 to 4 that said guard electrode extends is likewise streamlined in shape in this embodiment.

Figure 1:
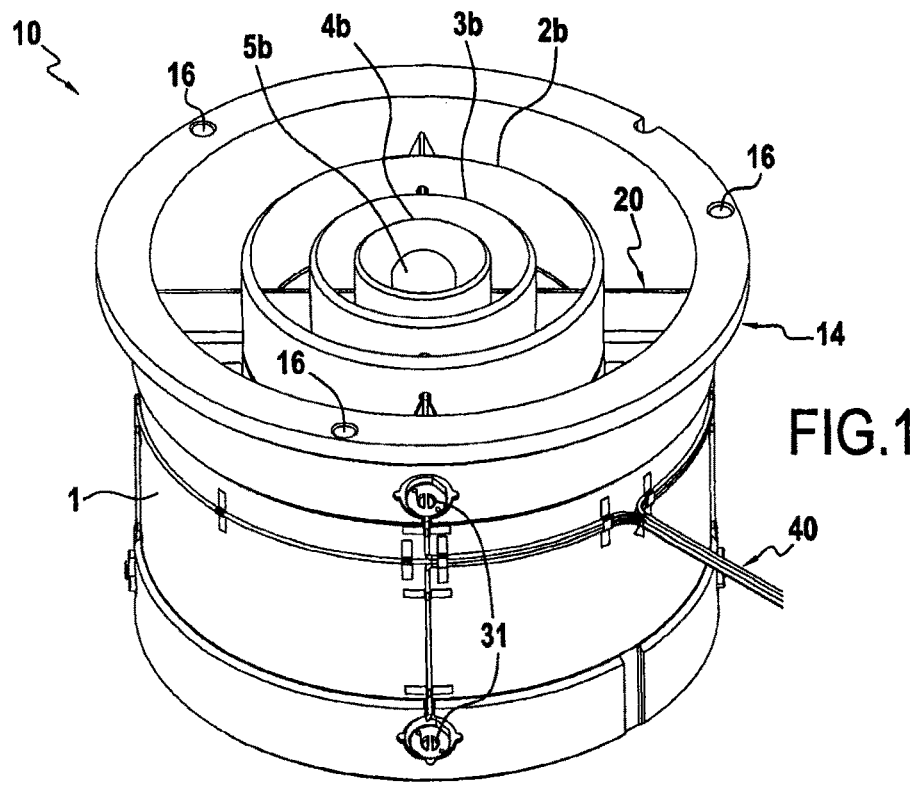
FIG. 1 is a perspective view showing the sleeve of a sensor in accordance with the present invention.

Furthermore, as shown in particular in FIG. 1, at least the spacers 20 at the upstream end of the sleeve 10 (and in particular also the spacers 20 at the downstream end of the sleeve 10) are also streamlined.

In particular, each spacer 20 is substantially triangular in section with an apex in alignment with the radial plane representing the direction in which said spacer 20 extends, and it points in the axial direction away from the end at which the measurement electrodes 2 to 4 are located.

There follows a description of the various steps involved in assembling the sleeve 10 of the sensor in a workshop.

The first step consists in passing the connection wires 40 from the outside through the orifices of the outer body 1 of the sleeve 10.

For each spacer 20, the second step consists in passing the corresponding connection wires 40 along the passage 25 in said spacer 20 and causing each connection wire 40 to exit through that one of the opening portions of said passage 25 that corresponds thereto so as to enable the wire 40 to penetrate into that one of the subdivision spaces A to D that is associated therewith.

The third step consists in causing the four first holder rods 30 to pass respectively through the four upstream spacers 20 of the sleeve 10, in screwing said rods 30 to the first segment 5 of the central core, and in screwing the corresponding nuts 31 against the outer body 1.

The fourth step consists in inserting the third intermediate measurement electrode 4 into the sleeve 10 and fastening it therein, in inserting the associated guard electrode 4b in the upstream end of the sleeve 10 and fastening it therein, and in connecting the corresponding connection wires 40 penetrating from the associated spacers 20.

The fifth step consists in repeating the fourth step for the second intermediate measurement electrode 3 and its associated upstream guard electrode 3b, and then for the first intermediate measurement electrode 2 and its associated upstream guard electrode 2b.

The sixth step consists in positioning the shim of the central core against its first segment 5, in positioning the second segment 5a, and in fastening these two segments together by means of the screw 12.

The seventh step consists in passing the four last holder rods 30 respectively inside the four downstream spacers 20 of the sleeve 10, in screwing said rods 30 to the second segment 5a of the central core, and in screwing the corresponding nuts 31 against the outer body 1.

The last step consists in putting into place the three downstream guard electrodes 2a to 4a of the sleeve 10 in a manner analogous to that described for the fourth and fifth steps.

There follows a description of the switch and measurement members 50 in accordance with the present invention.

In the embodiment shown, the sensor is a capacitive sensor.

In this embodiment, the fluid flowing in the flow line is an electrically insulating two-phase fluid.

Figure 6:
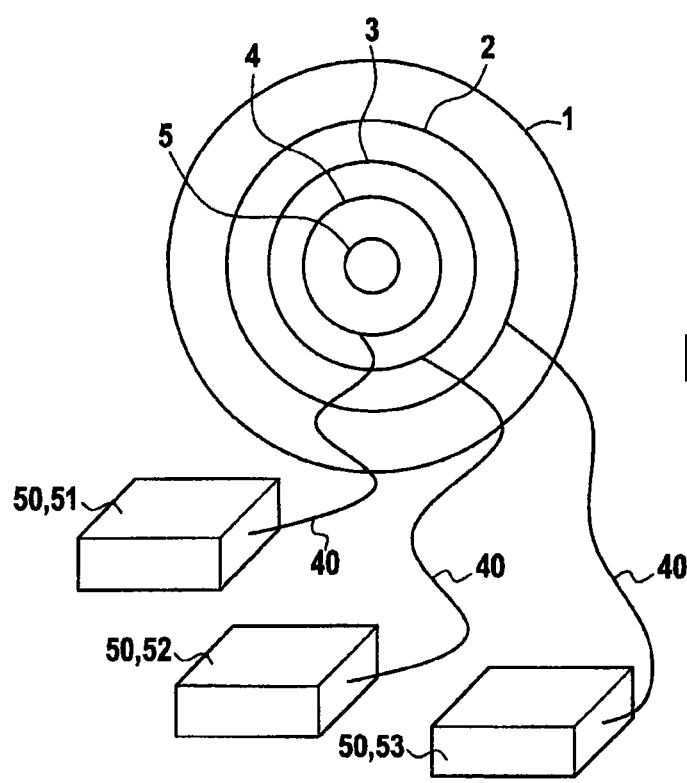
FIG. 6 is a diagrammatic view of said sleeve coupled to switch and measurement members in accordance with the present invention.

As shown in FIG. 6, the switch and measurement members 50 comprise one or more capacitive conditioners (specifically three conditioners 51 to 53) that are separate from one another and that may be connected optionally to one, to several, or to each of the measurement electrodes of the sleeve 10 (in particular to the three intermediate measurement electrodes 2 to 4 via respective connection wires 40).

Each conditioner 51 to 53 has a first voltage generator that delivers a first voltage V1; and a second voltage generator that delivers a second voltage V1' that is independent of the first voltage V1 but that is at all times identical thereto.

In particular, the first generator is configured so that the first voltage V1 that it delivers is variable under steady conditions at a frequency f1, with an amplitude A1, and a phase P1.

Likewise, the second generator is configured so that the second voltage V1' that it delivers is variable under steady conditions at a frequency f1', with an amplitude A1', and with a phase P1', and that at all times satisfies the following three conditions: f1'=f1; A1'=A1; and P1'=P1.

In addition, each conditioner 51 to 53 has a switch circuit configured to switch between:
- a first state E1 in which said conditioner delivers the first voltage V1 at a first output and the second voltage V1' at a second output; and
- a second stage E0 in which the first and second generators of said conditioner are short circuited so that said first and second outputs both deliver a short-circuit voltage corresponding to a fixed potential V0 of said conditioner, in particular sensor ground.

Each conditioner 51 to 53 also has a circuit for measuring the current delivered by said first generator.

In addition, the lines at the fixed potential V0 of each of the conditioners 51 to 53 are connected together so that they deliver identical short-circuit voltages in their respective second states E0.

The conditioners 51 and 53 are also synchronized so that the voltages V1 and V1' that they deliver when they are in their respective first states E1 have the same phases at all times.

Likewise, the conditioners 51 to 53 are selected so that when they are in their respective first states E1, the voltages V1 and V1' that they deliver present amplitudes and frequencies that are as close together as possible, and in theory amplitudes and frequencies that are identical.

The switch and measurement members 50 are coupled to the measurement electrodes 1 to 5, in particular via the above-described connection wires 40.

More particularly, the two furthest-apart measurement electrodes 1 and 5 of the sleeve 10 are both electrically connected to the same line at the fixed electrical potential V0 as each of the conditioners 51 to 53 (in particular at sensor ground potential, which is then common to the switch and measurement members and to the sleeve).

The respective first outputs of the three conditioners 51 to 53 are connected respectively to the three intermediate measurement electrodes 4, 3, and 2.

In this embodiment, the switch and measurement members 50 are coupled to the guard electrodes 2a to 4a and 2b to 4b, in particular via the above-described connection wires 40, so that said guard electrodes are at the same electrical potential at all times as the measurement electrodes 2 to 4 that they extend respectively.

For this purpose, the respective second outputs of the three conditioners 51 to 53 are connected respectively to the three upstream guard electrodes 4b, 3b, and 2b of the sleeve 10, and to the three downstream guard electrodes 4a, 3a, 2a of the sleeve.

It can thus be understood that the switch and measurement members 50 are suitable for controlling the switching of each subdivision space A to D within the sleeve 10 between a measuring state and a non-measuring stage.

More precisely, said measuring state of a subdivision space under consideration is obtained when as a result of the switching performed by the conditioners 51 to 53 between their respective first and second states E1 and E0, the first voltage V1 is applied to a first one of two adjacent measurement electrodes defining said subdivision space under consideration, while the fixed potential V0 is applied to the other one of said two adjacent measurement electrodes, such that an excitation electrical signal corresponding to the potential difference V1–V0 is applied between said two adjacent measurement electrodes.

In addition, in said measuring state of said subdivision space under consideration, the measurement circuit of the conditioner that is connected to said first one of the two adjacent measurement electrodes measures the electric current delivered by the first generator of said conditioner as the value representative of the electrical signal received as a result of applying said excitation electrical signal, so as to be able to determine the gas content of the fluid that is associated with the representative value.

Furthermore, said non-measuring state of a subdivision space under consideration is obtained when the switching of the conditioners 51 to 53 between their respective first and second states E1 and E0 causes both of the two adjacent measurement electrodes defining said subdivision space under consideration to be at the same potential V1 or V0.

Furthermore, since the conditioners 51 to 53 are separate, each of them may switch between its first state E1 and its second state E0 independently of the other conditioners 51 to 53.

It can thus be understood that the switch and measurement members 50 are configured to selectively switch the states of each of the subdivision spaces A to D independently of one another.

Furthermore, the conditioners 51 to 53 may be controlled, e.g. by computer, so as to define a measurement cycle during which said conditioners sequentially switch the state of at least one of the subdivision spaces A to D at least once.

For example, it is possible to perform the measurement cycle that is described below.

During a first time interval t1 of the measurement cycle, the switches of the conditioners are used to apply the following potentials to the measurement electrodes 1 to 5 of the sleeve 10 of the sensor:

|  | Measurement electrode | | | | |
| --- | --- | --- | --- | --- | --- |
|  | 1 | 2 | 3 | 4 | 5 |
| Potential | V0 | V1 | V1 | V1 | V0 |

It can thus be seen that the excitation voltage V1–V0 is applied between the two adjacent electrodes 1 and 2 defining the first subdivision space A. Consequently, this first space A is in its measuring state.

The corresponding conditioner measures the current delivered by its first generator.

Given that the two electrodes 2 and 3 defining the adjacent subdivision space B are both at the same potential V1, said adjacent space B is in its non-measuring state.

Consequently, the current delivered to the measurement electrode 2 is representative only of the reception voltage that results from the application of the excitation voltage that is applied between the two adjacent electrodes 1 and 2. As a result, the measured electric current has an amplitude and/or a phase shift relative to the amplitude and phase of the voltage V1 delivered by the first generator of the corresponding conditioner, which present values that depend directly on the dielectric constant of the fluid flowing specifically in the first subdivision space A. Thus, during this first time interval t1, it is possible to determine directly the gas bubble content forming specifically in the first subdivision space A.

The same applies to the fourth subdivision space D since an excitation voltage V1–V0 is likewise applied between the two adjacent electrodes defining said space D, whereas the adjacent subdivision spacer C is in its non-measuring state.

To sum up, during this first time interval t1, the gas bubble contents that are formed specifically in the first subdivision space A and in the second subdivision space D are both obtained simultaneously.

Thereafter, during a later second time interval t2 of the measurement cycle, the state of the conditioner 53 that is connected to the second measurement electrode 2 is switched on its own, this conditioner going from its first state E1 to its second state E0. The following configuration is then obtained:

|  | Measurement electrode | | | | |
| --- | --- | --- | --- | --- | --- |
|  | 1 | 2 | 3 | 4 | 5 |
| Potential | V0 | V0 | V1 | V1 | V0 |

Thus, during this second time interval t2, the gas bubble contents that are formed specifically in the second subdivision space B and in the fourth subdivision space D are obtained simultaneously.

Thereafter, during a subsequent third time interval t3 of the measurement cycle, the state of the conditioner 53 connected to the second measurement electrode 2 is switched so that it passes from its second state E0 to its first state E1, and likewise the state of the conditioner 51 that is connected to the fourth measurement electrode 4 is switched so that it passes from its first state E1 to its second state E0. The following configuration is then obtained.

| Measurement electrode | | | | |
|---|---|---|---|---|
| 1 | 2 | 3 | 4 | 5 |
| Potential V0 | V1 | V1 | V0 | V0 |

Thus, during this third time interval t3, the gas bubble contents that are formed specifically in the first subdivision space A and in the second subdivision space C are both obtained simultaneously.

It can thus be understood that with only three operations of switching the conditioners during a simple three-step sequence, it is possible to determine the gas bubble contents that form specifically in each of the subdivision spaces A to D of the flow section of the sleeve 10 of the sensor, each of the spaces A to D adopting its respective measuring states at least once during the measurement cycle.

Furthermore, it should be observed that in this measurement cycle example, the subdivision spaces A and D adopt their respective measuring states more often than do the other two subdivision spaces B and C (in particular twice each instead of once each).

Furthermore, the measurement cycle may advantageously, but not necessarily, include at least one fourth step of verifying the linearity of the measurements of the sensor.

More particularly, a fourth time interval t4 subsequent to the third time interval t3 may be added to the measurement cycle, with the following configuration being obtained during the time interval t4:

| Measurement electrode | | | | |
|---|---|---|---|---|
| 1 | 2 | 3 | 4 | 5 |
| Potential V0 | V1 | V0 | V1 | V0 |

Thus, during this fourth time interval t4, the first and second subdivision spaces A and B, which are adjacent, are both in their measuring states.

As a result, the current delivered by the conditioner 53 that is connected to the second measurement electrode of the sleeve, i.e. the electrode that is common to both of the spaces A and B, has a first component that is representative of the dielectric constant of the first space A, and a second component that is representative of the dielectric constant of the second space B. It can thus be understood that the measurement current measured by said conditioner 53 serves to determine the gas bubble content that is formed in the combined space A+B constituted both by the first space A and by the second space B.

Similarly, the current measured by the conditioner 51 that is connected to the fourth electrode 4 during this fourth time interval t4 serves to determine the gas bubble content that is formed in the combined space C+D constituted both by the third space C and by the fourth space D.

Likewise, the current measured by the conditioner 52 that is connected to the third electrode 3 during this fourth time interval t4 serves to determine the gas bubble content that is formed in the combined space B+C constituted both by the second space B and by the third space C.

The invention claimed is:

1. A sensor for determining gas content of a two phase fluid flowing in a flow line, the sensor comprising:
    a sleeve configured to be arranged in the flow line, in a stream of the fluid, wherein the sleeve of the sensor includes a plurality of measurement electrodes spaced apart from and in register with one another so that in pairs the measurement electrodes define a plurality of subdivision spaces subdividing a flow section of the sleeve; and
    switch and measurement members that are coupled to the measurement electrodes to cause each subdivision space of the sleeve to switch between a measuring state in which the members apply an excitation electrical signal between the two adjacent measurement electrodes defining a subdivision space under consideration and measure a value representative of a reception electrical signal resulting from applying the excitation electrical signal to determine gas content of the fluid that is associated with the representative value, and a non-measuring state,
    wherein the switch and measurement members are configured to selectively switch the state of each of the subdivision spaces independently of one another, and
    wherein the sleeve of the sensor further includes guard electrodes that extend ends of the measurement electrodes while being electrically separate therefrom, and that are coupled to the switch and measurement members such that the guard electrodes are at all times at a same electric potential as the measurement electrodes that the guard electrodes extend respectively.

2. A sensor according to claim 1, wherein the switch and measurement members apply a same electric potential to the two adjacent measurement electrodes that define the subdivision space under consideration to cause the space to adopt the non-measuring state.

3. A sensor according to claim 1, wherein the switch and measurement members interrupt all electrical connections between the two adjacent measurement electrodes defining the subdivision space under consideration to cause the space to adopt the non-measuring state.

4. A sensor according to claim 1, wherein the switch and measurement members sequentially switch the state of at least one of the subdivision spaces at least once during a measurement cycle.

5. A sensor according to claim 4, wherein each subdivision space adopts the measuring state at least once during the measurement cycle.

6. A sensor according to claim 4, wherein during the measurement cycle at least a first of the subdivision spaces adopts the measuring state while another subdivision space adjacent to the first adopts the non-measuring state.

7. A sensor according to claim 1, wherein the measurement electrodes are spaced apart from one another by spacers at least partly made of electrically insulating material.

8. A sensor according to claim 7, wherein the spacers include passages into which connection wires are inserted to provide the coupling between the measurement electrodes and the switch and measurement members.

9. A sensor according to claim 1, wherein the measurement electrodes are plane and parallel to one another.

10. A sensor according to claim 1, wherein the measurement electrodes are coaxial, surrounding one another about a common axis, and presenting a section that is circular in a section plane perpendicular to the common axis.

11. A sensor according to claim 10, wherein the measurement electrodes are frustoconical.

12. A sensor according to claim 10, wherein the measurement electrodes are cylindrical.

13. A sensor according to claim 10, wherein a ratio of diameters of two adjacent measurement electrodes in the section plane lies in a range of 1.1 to 3.0, or in a range of 1.4 to 2.0.

14. A sensor according to claim 1, wherein the sleeve has three to six measurement electrodes.

* * * * *